US005697922A

United States Patent [19]
Thombre

[11] Patent Number: 5,697,922
[45] Date of Patent: Dec. 16, 1997

[54] DELIVERY DEVICE HAVING ENCAPSULATED EXCIPIENTS

[75] Inventor: Avinash G. Thombre, Dover, N.J.

[73] Assignee: Pfizer Inc., New York, N.Y.

[21] Appl. No.: 424,476

[22] PCT Filed: Oct. 13, 1993

[86] PCT No.: PCT/US93/09582

§ 371 Date: May 11, 1995

§ 102(e) Date: May 11, 1995

[87] PCT Pub. No.: WO94/12152

PCT Pub. Date: Jun. 9, 1994

Related U.S. Application Data

[63] Continuation of Ser. No. 979,727, Nov. 20, 1992, abandoned.

[51] Int. Cl.[6] ............................................. A61K 9/22
[52] U.S. Cl. ............................. 604/892.1; 424/473
[58] Field of Search ....................... 604/891.1, 890.1, 604/892.1; 424/422–424, 453, 458–460, 468–473, 456, 461, 462, 463, 477, 478, 479, 482

[56] References Cited

U.S. PATENT DOCUMENTS

| | | | |
|---|---|---|---|
| 4,111,201 | 9/1978 | Theeuwes | 424/473 |
| 4,111,203 | 9/1978 | Theeuwes | 604/892.1 |
| 4,608,048 | 8/1986 | Cortese et al. | 604/892.1 |
| 4,755,180 | 7/1988 | Ayer et al. | 604/892.1 |
| 5,120,548 | 6/1992 | McClelland et al. | 424/473 |
| 5,225,202 | 7/1993 | Hodges et al. | 424/480 |
| 5,260,068 | 11/1993 | Chen | 424/451 |

FOREIGN PATENT DOCUMENTS 0357369  3/1990  European Pat. Off. .

OTHER PUBLICATIONS

G. A. McClelland et al, "The Solubility–Modulated Osmotic Pump: In vitro/In vivo Release of Diltiazem Hydrochloride", Pharma. Research, vol. 8, No. 1, pp. 88–92 (1991).

*Primary Examiner*—Michael Powell Buiz
*Assistant Examiner*—At Nguyen
*Attorney, Agent, or Firm*—Peter C. Richardson; Gregg C. Benson; A. Dean Olson

[57] ABSTRACT

An asymmetric membrane, osmotic, delivery device having coated macroparticulate solubility modifiers. The device comprises a beneficial agent, an osmagent, a coated macroparticulate solubility modifier and an asymmetric membrane that surrounds the device components. The device is useful for dispensing a beneficial agent to an aqueous environment of use. The coated macroparticles modify the solubility of the beneficial agent so that it's release can be controlled. The larger size of the solubility modifier macroparticles provides, for example, a longer release duration than would have been possible with a smaller size.

8 Claims, 6 Drawing Sheets

DELIVERY DEVICE HAVING ENCAPSULATED EXCIPIENTS

BACKGROUND OF THE INVENTION

This application was filed under 35 U.S.C. §371 based on PCT/US93/09582, which was filed on Oct. 13, 1993 which is a continuation of U.S. application Ser. No. 07/979,727 which was filed on Nov. 20, 1992 and is now abandoned.

This invention relates to devices useful for the delivery of a beneficial agent to an environment of use.

There are a variety of delivery devices that incorporate osmagents in the device core. The osmagents cause an osmotic pressure gradient across the device wall and imbibe fluid into the device. Such delivery devices release their active agents either by osmotic pumping or by diffusion or by a combination of the two mechanisms. Since the active agent is released from the device as an aqueous solution, the release rate is dependent on the solubility of the active agent in water. This release rate dependence on the solubility of the active agent can inhibit the attainment of a preferred release rate profile. In order to obtain a useful release profile for poorly water soluble beneficial agents, a solubility enhancing agent may be added to the device core. Alternatively, to obtain a useful release profile for highly water soluble active agents, an excipient which decreases the active agent solubility may be added to the device core.

U.S. Pat. No. 4,755,180 ('180) describes such solubility modifying excipients and discloses coating of the excipients with a polymer coating in order to control the release of the excipient. The '180 patent discloses "osmagents" (beneficial agent solubility modifying agents) having various forms such as particles, powders and the like. Generally, the release rate controlling film has a thickness of 1 to 20 mils, and in a preferred embodiment, has a thickness of 2 to 10 mils. In addition, McClelland, Gregory A., Sutton, Steven C., Engle, Karen, and Zentner, Gaylen, M. "The Solubility-Modulated Osmotic Pump: In Vitro/in Vivo Release of Diltiazem Hydrochloride", Pharmaceutical Research, Vol. 8, No.1. (1991) disclosed the design and evaluation of a solubility-modulated controlled-porosity osmotic pump for delivery of the highly water-soluble drug diltiazem hydrochloride. Specifically, the study incorporated coated sodium chloride crystals (i.e., microosmotic pumps) into the core tablet formulation of a diltiazem hydrochloride controlled porosity osmotic pump. This pump-in-a-pump design prevented the rapid depletion, and large attendant concentration variation, of the solubility modulating agent (sodium chloride) within the diltiazem hydrochloride core tablet environment. Thus, the release of the solubility modulator was controllable and, was designed to provide modulation of the drug solubility for a prolonged period.

In another aspect of delivery devices, the use of an asymmetric membrane to coat the device core has been disclosed (E.P.O. Publication No. 0357369). That publication discloses an asymmetric membrane having two regions or membrane layers. The substructure is relatively thick and very porous in nature. This substructure supports the other portion of the membrane, a dense, thin skin.

Although there has been a significant advance in the field of controlled delivery devices, there is a continuing search for other delivery devices, particularly those which deliver poorly water soluble or highly water soluble beneficial agents.

SUMMARY OF THE INVENTION

This invention is directed to an asymmetric membrane delivery device having coated, macroparticulate, beneficial agent- solubility modifiers for use in dispensing a beneficial agent to an aqueous environment of use. The device comprises a beneficial agent, an osmagent, a macroparticulate solubility modifier and an asymmetric membrane that surrounds the device components. The solubility modifier is coated. The solubility modifier or beneficial agent may be the osmagent or there may be a separate osmagent.

Another aspect of this invention is a method for the delivery of a beneficial agent to an environment of use which comprises placing the above device into the environment of use.

These devices enable the control of the beneficial agent release profile. In particular, the large sized coated excipients provide significant advantages over smaller sized coated excipients such as facilitating the use of a greater variety of coating materials. Thus, they make a significant advance in the field of delivery devices. Other objects, features, and advantages of the invention will be more apparent to those skilled in the art from the following detailed specification, taken in conjunction with the figures and the accompanying claims.

DETAILED DESCRIPTION OF THE INVENTION

Figure 1:
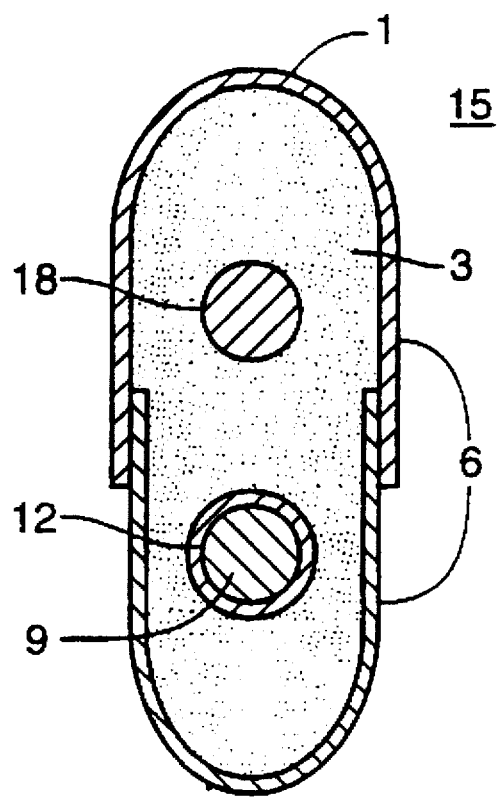
FIG. 1 discloses a schematic cross-sectional view of an exemplary device of the invention.

Any material may be used to modify the solubility of the beneficial agent that is appropriate for the proposed delivery device use. This material may also function as the osmagent or a separate osmagent may be used. The solubility change can be due to pH, i.e., when the excipient is an acid or alkaline agent or a buffer, or it can be due to a common-ion effect, or by any other mechanism. Preferably the solubility modifier increases the solubility (in the aqueous environment) of a beneficial agent exhibiting low solubility (i.e., less than about 5 mg/ml) or decreases the solubility (in the aqueous environment) of a beneficial agent exhibiting high solubility (i.e., greater than about 300 mg/ml). It is especially preferred that a solubility modifier is used that provides a predetermined beneficial agent solubility and consequently a predetermined beneficial agent release profile (i.e. controlled release).

Any osmagent may be used that is appropriate for the desired application. As stated above, the solubility modifier may also act as the osmagent or there may be a separate osmagent. In fact the beneficial agent (described below) may also act as the osmagent, by itself, or in combination with the solubility modifier. For example, the solubility modifier may alter the solubility of the beneficial agent causing it to act as the osmagent. It is intended that the above embodiments are within the scope of the invention. The osmagent is a substance which, in solution, exhibits a certain osmotic pressure that is the driving force for water ingress into the device (this increases the internal hydrostatic pressure resulting in release of a substance through a barrier membrane). Preferably the osmagent increases the osmotic pressure to above about seven atmospheres which is the normal pressure in mammalian body fluids. As stated before, one component may function as both the osmagent and the solubility modifier or there can be a combination of components. For example, certain substances such as magnesium carbonate hydroxide, affect the pH, and, thus the solubility of the beneficial agent but are not substantially soluble themselves in the aqueous solution, and thus, do not appreciably affect the osmotic pressure. Exemplary osmotic agent/solubility modifiers include: sugars such as sucrose, lactose, mannitol, maltose, sorbitol and fructose; neutral salts such as sodium chloride, magnesium sulfate, magnesium chloride, potassium sulfate, sodium carbonate, sodium sulfite, potassium acid phosphate, sodium acetate and ethyl acetate; acidic components such as fumaric acid, maleic acid, adipic acid, citric acid and ascorbic acid; alkaline components such as tris(hydroxylmethyl) aminomethane (TRIS); meglumine, tribasic and dibasic phosphates of sodium and potassium; amino acids such as glycine and arginine; and other compounds such as urea. The colligative properties of these substances such as osmotic pressures, and other physicochemical properties such as solubility, pKa, etc. are given in several handbooks and reference books (e.g., Handbook of Chemistry and Physics, The Merck Index, etc.).

Preferred osmagent/solubility modifiers include acidic and alkaline agents such as fumaric acid, citric acid, TRIS and meglumine.

By macroparticulates is meant the coated excipients are 0.16 cm to 1.27 cm in diameter. It is especially preferred that the coated excipients are about 0.48 cm to 0.64 cm in diameter. These sizes differentiate the coated excipients from the fine powders or crystals that have been used previously as described in the Background Art. It is also preferred that the macroparticulates comprise from about 10% to about 90% by weight of the core of the device. Preferably two to four macroparticulates are used. These sizes provide various advantages such as facilitating the choice of a wide variety of polymer coatings. For example, only a few types of coatings can be used to provide prolonged (e.g. twelve hour duration) release coating from very small core particles because the coatings would have to possess a very low permeability. Further-more, if a very thick coating is used to achieve the low permeability, it is possible that some of the excipient in the solubility modifier core would be adsorbed to the coating and not released. Alternatively stated, because of the inherent geometry, a larger macroparticulate can use a thinner coating relative to a smaller particulate to achieve prolonged release, with a less probability that the excipient is trapped in the heavy coating. Another advantage of the macroparticulates is that they are significantly easier to coat than the smaller granules used by the prior art. Yet another advantage is that because of surface area/volume considerations, the use of macroparticulates allows the use of a lower coating weight, thereby conserving materials, allowing the coating operation to be finished in a reasonable period of time (i.e., manufacturability), and providing more flexibility with respect to the dose and amount of excipients that can be incorporated into a reasonable sized device. Another advantage resulting from the macroparticulates is that the solid undissolved solubility modifier persists for a longer period of time in the macroparticulate core which provides a constant gradient for water intake or water ingress into the core of the macroparticulate as well as drug release for a longer period of time. Thus, this results in more effective utilization of the excipient.

Any coating (e.g. film, membrane) may be used to surround the solubility modifier/osmagent that is appropriate for: the desired application. Preferably, the coating provides a predetermined release profile for the solubility modifier. It is preferred that the excipient coating provides a release profile having a predetermined time lag. Particularly preferred time lags are from 1 to 10 hours. This is particularly beneficial for those devices where the formulation, by itself, would have released incompletely, but with the solubility modifier present during the final release period, completely releases the beneficial agent is achieved. This is also beneficial when a time lag before drug release is desired. For example, a time lag before the onset of drug release may be beneficial because it would protect a drug which was susceptible to degradation in the acidic environment of the stomach. Such a device would also be useful in providing repeat-action or pulsatile delivery, i.e., periods of no drug release in between periods of drug release at a predetermined rate and over a predetermined duration. Two or more solubility modifier coated macroparticulates having different time lags may be combined to achieve the desired beneficial agent release profile. This, of course, could include the use of two different solubility modifier compounds coated to give the desired time lags. Time lag release coatings are known in the art and may be achieved by a number of mechanisms. For example the time lag may be caused by the use of traditional enteric coatings or slowly dissolving polymers. They may also, at least partially, be caused by the delay in water penetration into the device through the device coat and then into the coated macroparticulate excipient formulation through the excipient coating. Thus, this coating does not necessarily have to dissolve at high pH as is the case with the "traditional" enteric polymers. Time lag release coatings may also be achieved by the use of other mechanisms such as osmotic bursting and chemical degradation of the coating (e.g., hydrolysis). Time lag release coatings may be achieved by varying the coating thickness, coating composition, surface area and size, coating permeability and/or weight proportion of macroparticulate to the device core. For example, by increasing the ratio of polymer to hydrophilic plasticizer (pore former), the time lag is increased (e.g., the higher the proportion of cellulose acetate to polyethylene glycol the longer the time lag will be).

It is also preferred that the excipient coating provides a release profile that yields a predetermined excipient release duration. Particularly preferred excipient release durations are from 4 to 24 hours. This is particularly beneficial for those devices where the formulation, by itself, would have released incompletely but with the solubility modifier present during the final release period, completely releases the beneficial agent. This duration modification may be achieved in analogous manners to that used to achieve the time lag.

It is also preferred that the excipient coating provides a release profile that yields a predetermined excipient release rate profile (e.g. constant, increasing, decreasing). This, in turn, would provide the corresponding predetermined release rate profile for the active agent (e.g., constant, increasing, or decreasing). In most cases, a constant release rate profile of the beneficial agent is desired to maximize the duration of therapeutic concentrations. However, in some cases, for example, in order to take advantage of chronopharmacokinetics or, depending on the natural progression of the disease for which treatment is sought or, in devices that have a biofeedback loop incorporated in them, decreasing or increasing release profiles may be preferred.

It is also preferred that a combination of coated excipients such as those described above and uncoated excipients be used as this enables the further tailoring of the beneficial agent release profile. Thus, in this case, the uncoated excipient will be available to perform its function at early times without any time-lag while the excipient that is coated will be available at later times, or over a prolonged period of time.

A predetermined release profile (e.g., release kinetics, time-lag, and extent of release) for the solubility modifier can also be achieved by means other than coated macroparticulates. Thus, the solubility modifer can be formulated as a matrix tablet with hydrophilic polymers (e.g., hydroxypropylcellulose, hydroxypropylmethyl cellulose, etc.) which operates by a diffusion-dissolution and/or an erosion mechanism. Other release mechanisms such as diffusion through barriers in series, osmotic bursting, etc., can also be utilized to affect the release profile of the solubility modifier. Polymers which have a pH dependent solubility (e.g., cellulose acetate phthalate, hydroxypropylmethylcellulose phthalate etc.,) and those (e.g., poly(ortho esters), polyanhydrides etc.) that degrade chemically (e.g., by hydrolysis and oxidation) can also be used to achieve a predetermined release profile for the solubility modifier by means that are well known in the art of controlled release.

The rate of release of solubility modifier may be determined by techniques known in the art such as are described in U.S. Pat. No. 4,755,180.

Preferably the macroparticulate coating is made from a film-forming polymer with appropriate permeability characteristics (e.g., water-insoluble film-forming polymers such as cellulose derivatives). The molecular weight or molecular weight distribution of the polymers is such that coatings made from these polymers have adequate mechanical properties for the desired application. Typical polymer types include olefin and vinyl-type polymers, condensation-type polymers, addition type polymers, organo-silicon polymers, etc. Particularly preferred polymers include polyacrylics, polyethylenes, polysulfones, polyamides, polyurethanes, polypropylene, ethylene-vinyl acetate, polyvinyl chloride, polyvinyl alcohol, ethylenevinyl alcohol, polyvinylidene fluoride, glycols, polyethylene glycol and polymethyl methacrylate. Copolymers of the above polymers such as copolymers of acrylic and methacrylic acid (Eudragit polymer line, Rohm Pharma, Germany) may also be used. The polymers can also include fats, waxes and silicone elastomers. It is especially preferred that the cellulose esters and cellulose ethers are used. Examples include cellulose acetates (acetyl content varying from 31% to 43.9% corresponding to a degree of substitution from 2.1 to 2.9) and cellulose acetate butyrates (butyl content from 17% to 50%) and blends of cellulose acetates and cellulose acetate butyrates. These are generally commercially available from Eastman Chemicals, Kingsport, Tenn., FMC Corporation, Philadelphia, Pa., and Dow Chemicals, Midland, Mich. In addition, cellulose ethers such as ethylcellulose and blends of cellulose ethers and cellulose esters such as methylcellulose, ethylcellulose-cellulose acetate and ethylcellulose-acetate butyrate are preferred. Other soluble polymers such as hydroxypropyl methylcellulose (HPMC), hydroxypropyl cellulose (HPC), hydroxyethyl cellulose, sodium carboxymethylcellulose and polyvinylpyrrolidone can also be used. The molecular weight (typically measured by viscosity) of the polymer is preferably sufficient to provide the mechanical properties appropriate for the particular application.

In addition, to the film forming polymer, the macroparticulate coating can also contain other materials such as plasticizers, pore-formers, dyes, etc. Plasticizers reduce the brittleness of polymer films, and increase their flexibility and mechanical strength, and alter their permeability. Plasticizers can be chosen from the following hydrophilic and hydrophobic materials: glycerine, polyethylene glycols (available as Carbowax from Union Carbide, Danbury, Conn. with nominal molecular weights ranging from 200 to 8000), polypropylene glycols, polyvinylpyrrolidone, methylcellulose, hydroxypropylmethylcellulose, glyceryl stearate, triethylcitrate, tributylcitrate, dibutyl sebacate, diethyl phthalate, acetyl tributyl acetate, triacetin acetylated monoglycerides, castor oil and soybean oil.

Although the solubility modifier coating can have any structure or be made of any material that controls the release profile of the solubility modifier, it is preferred that the coating be a polymeric coating that becomes permeable to the excipient upon exposure to the aqueous environment. For example, in one embodiment, the water soluble component that is added to the film forming polymer may be out leaving a porous membrane. Alternatively, the macroparticulate coating can be asymmetric (as described below) or dense. Generally, depending on the process used to make the coating, it can have a layered (stratified) structure as in layers of asymmetric membrane or layers of dense membranes. The coating can also be semipermeable, i.e., permeable to water but not the solubility modifier. This results in primarily an osmotic delivery mode. The coating can also have one or more holes (between 100 μm and 2 mm) or many macro (1 to 100 microns) and micro (less than 1 micron) pores. Coatings having a combination of micro- and macro-pores can also function by osmotic pumping since water ingress into the device can be via the micro-pores and through the polymer while the excipient is pumped out from the macro-pores. Further, the coating can consist of a network of interconnected water-filled pores through which the excipient is released by diffusion. In general, the greater the number of larger pores, the more the contribution by diffusive delivery versus osmotic delivery. The pores can be formed as part of the manufacturing process. They can also be formed after exposure of the coated excipient to water due to leaching of a phase-separated water soluble component (solid or liquid) in the excipient coating or by sublimation of a component from the film, typically during the drying operation. The pores can also be formed by "osmotic bursting" by incorporation of a swellable component (e.g. hydrogel) in the device or through bursting of a weak portion of the coating. The weak portion can be intentionally built-in into the coating as part of the manufacturing process.

Preferably, 5–45% of the macroparticulate core weight is coating. Typically the macroparticulate coating is about 1 μm to 1 mm in thickness. Preferably the macroparticulate coating is about 10 μm to 300 μm in thickness. Preferably the pore size is 1 μm to 100 μm in diameter and the porosity void volume may vary from 20% to 95%. The hole size is preferably between 100 microns and 1.5 mm.

The asymmetric membrane that surrounds the device core components may be any asymmetric membrane that provides the desired release profile for the particular application chosen. Asymmetric membranes are described in "The Use of Asymmetric Membranes in Delivery Devices" E.P.O.

Pub. No. 0357369 the U.S. equivalent of which is U.S. application Ser. No. 391,741, the disclosure of which is hereby incorporated by reference. Briefly, an asymmetric membrane is comprised of two regions of membrane layers. The substructure is relatively thick and very porous in nature. This substructure supports the other portion of the membrane, a very dense, thin skin. Generally, the asymmetric membrane dense skin is 3 μm to 6 μm and the substructure is 4 μm to 300 μm. Generally the overall thickness is from 10 μm to 300 μm. Typically this corresponds to 5% to 30% by weight based on the core weight. Typical polymers used in fabricating asymmetric membranes are cellulose derivatives, polysulfones, polyamides, polyurethanes, polypropylene ethylene-vinyl acetate polyvinylchloride, polyvinyl alcohol, ethylene vinyl alcohol, polyvinylidene fluoride and polymethyl methacrylate.

The beneficial agents used in the devices of this invention include, for example, any physiologically or pharmacologically active substance that produces a ocalized or systemic effect in animals including mammals (e.g., human beings). The beneficial agents, their therapeutic properties and their solubilities are known to the drug dispensing art in Pharmaceutical Sciences, by Remington, 15th. Ed., 1975 published by the Mack Publishing Co., Easton, Pa.; and in USAN and the USP Dictionary of Drug Names, Mary G. Griffiths Ed., 1985, published by USP Convention Inc., Rockville, Md.

Examples of active agents include inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autoacoid systems, alimentary and excretory systems, inhibitors of autocoids and histamine systems. The pharmaceutical agent that can be delivered for acting on these systems includes antidepressants, hypnotics, sedatives, psychic energizers, tranquilizers, anticonvulsants, muscle relaxants, antisecretories, antiparkinson agents, analgesics, anti-inflammatory agents, local anesthetics, muscle contractants, antibiotics, antimicrobials, anthelmintics, anti-malarials, hormonal agents, contraceptives, histamines, antihistamines, adrenergic agents, diuretics, antiscabiosis, anti-pediculars, antiparasitics, anti-neoplastic agents, hypoglycemics, electrolytes, vitamins, diagnostic agents and cardiovascular pharmaceuticals.

Also included in such active substances are prodrugs of the above-described drugs. Such drugs or prodrugs can be in a variety of forms such as the pharmaceutically acceptable salts thereof.

The term beneficial agent is also meant to include other substances for which it is desirable and/or advantageous to control delivery into an environment of use. Examples of such substances include fertilizers, algacides, reaction catalysts and enzymes.

In addition to the above-mentioned possible ingredients of the devices of this invention, other common pharmaceutical excipients may be present. Examples include viscosity modifiers, antioxidants, stabilizers, flavoring agents, binding agents, tablet disintegrants, lubricants, gildants, adsorbents, inert diluents, surfactants etc. Typical examples are: binding agents such as carboxymethyl cellulose, hydroxyethyl cellulose, acacia gum, guar gum, microcrystalline cellulose, starch sodium polyethylene glycols, corn syrup, sucrose, lactose, mannitol, calcium phosphate and ethyl cellulose; tablet disintegrants such as starch, microcrystalline cellulose, clays and sodium alginate; lubricants such as talc, polyethylene glycol, corn starch, sodium benzoate and sodium acetate; gildants such as microfine silicas, corn starch, microcrystalline cellulose and talc; adsorbents such as silicas and starches; and inert diluents such as lactose, dextrose, starch, microcrystalline cellulose, calcium phosphate, calcium sulfate, sucrose, mannitol, kaolin and magnesium aluminum sulfate.

The devices of this invention can also be administered within a capsule comprising a water soluble wall. For example, the devices can be manufactured to be of suitable size for inclusion either singularly or multiply within a gelatin capsule such that when the capsule dissolves the device(s) are released into the environment of use. While the devices to be included within a capsule can be of a variety of shapes, a preferred shape for such devices is spherical or substantially spherical. The exact number and size of such devices can and will be determined according to a variety of well know factors. For example, the environment of use, the beneficial agent or agents, the amount of beneficial agent and the rate of release are all factors to be considered in determining the size, shape, and number of devices to be included in such capsules as well as the composition of the capsule.

The dispensing device shape and dimensions can vary based on the particular application (e.g., tablet). Common exemplary shapes are spherical cylindrical, tablet-shaped and capsular-shaped. The dispensing device dimensions may vary with the desired application (e.g., cattle tablets, human tablets). The shape and size may also vary depending on the application so that, for example, the tablet is suitable depending on the quantity and rate of beneficial agent delivery which vary based on the application. Preferably the tablet is 0.16 cm to 1.27 cm in size and the beads are 0.2 mm to 2.5 mm in size. Typical capsule dimensions range from about 1 cm to about 2.54 cm in length and about 0.25 cm to about 1.1 cm in diameter for human health applications. For animal applications such as ruminal delivery to cattle, typical dimensions range from about 5.1 cm to about 10.2 cm in length and about 1.3 cm to about 3.1 cm inches in diameter.

Typically, the beneficial agent comprises up to 50% of the weight of the device, the solubility modifier macroparticulate comprises up to 90% of the weight of the device, the osmagent comprises up to 90% of the weight of the device and the other excipients comprise up to 50% of the weight of the device. Typically, the macroparticulate coating comprises 5% to 45% of the weight of the beneficial agent and solubility modifier macroparticulate. Typically, the asymmetric membrane comprises 5% to 30% of the weight of all the device components.

A clearer understanding of the devices of this invention may be had by reference to FIG. 1. In FIG. 1 the beneficial agent and other excipients 3 are surrounded by asymmetric membrane capsule halves 6. External to the device 1 is the environment of use 15 including the aqueous solution. Inside the capsule halves 6 is one compressed macroparticulate 9 having a coating 12 thereon and another compressed macroparticulate 18 which is uncoated.

Preferred devices include those with an asymmetric membrane coating comprising cellulose acetate/glycerine and optionally triethyl citrate surrounding the beneficial agent, cellulose acetate/polyethylene glycol coated macroparticulates and other excipients. It is especially preferred that the macroparticulates comprise meglumine (N-methyl glucamine). It is also preferred that the weight proportion of cellulose acetate to polyethylene glycol is about 1/1 to 10/1 and that the weight proportion of the coating to the macroparticulate core is about 5% to about 30%. It is especially preferred that there are 1 to 4 macroparticulates having a size of about 0.48 cm to 0.64 cm.

The devices of this invention having the above described desired characteristics may be made using the above described materials using the following processes and other conventional methods.

The coated macroparticulate particles of this invention are made by standard procedures such as wet or dry granulation of the desired formulation followed by compression into a tablet. Alternatively, compressed tablets of the desired formulation can be made by direct compression, i.e., without a granulation step prior to compression. Macroparticulates (in the form of beads, spheres, or rounded shapes) may also be prepared by an extrusion-spheronization process in which the desired blend is wet-massed, extruded in an extruder (e.g., Luwa EXKS-1 extruder, LCI, Charlotte, N.C. or the Calera Model 40 extruder G.B. Caleva Ltd., Dorset, England), spheronized in a spheronizer (e.g., Luwa QJ-230 marumerizer, LCI, Charlotte, N.C. or the Calera Model 15 spheronizer, G.B. Caleva Ltd., Dorset, England), and the resulting macroparticulates dried by tray drying in a forced-air convection oven, fluid bed dryer, or vacuum dryer. Other drying methods such as microwave drying can also be used.

The macroparticulates are then optionally film-coated according to standard procedures with the desired coating by repeatedly dipping them into a coating solution and drying in-between dippings or, on a larger scale, by using conventional or side-vented coating pans (e.g., the Accela-Cota, Thomas Engineering, Hoffman Estates, Ill., the Vector-Freund Hi-Coater, Marion, Iowa, and the Driacoater, Driam USA, Spartanburg, S.C.). Alternatively, fluid-bed coating equipment with top-spray (granulator), bottom spray (Wurster), and tangential spray (rotor-processor) can also be used to apply the film-coat onto the macroparticulates. Such fluid-bed coating equipment is available from vendors such as Glatt Air Techniques, Ramsey, N.J. and from Aeromatic Inc., Columbia, N.J., and Vector Corporation, Marion, Iowa.

The active agent formulation in the present invention can simply be a homogeneous blend of the active agent and other excipients achieved by mixing or it can be a granulation prepared by standard dry or wet granulation techniques. In a wet-granulation technique, a blend of the dry components is wet-massed with water or with nonaqueous solvents. The wet mass is then dried and milled to achieve the desired particle size distribution.

Capsule formulations may be prepared by forming a cap and body of the above-described polymers. In a conventional fashion polymers may be molded into the desired shapes and sintered followed by dip-coating with an asymmetric membrane. Alternatively hard gelatin capsules may be coated with the asymmetric membrane. These semipermeable capsule bodies and caps are then filled with the beneficial agent, macroparticulates and other excipients using standard capsule filling techniques. Then, the capsule is sealed and assembled according to standard techniques. This may be performed using conventional capsule-sealing equipment. Tablets may be prepared using conventional processes and conventional tabletting and tablet-coating equipment. The tablet cores can be made by direct compression of the beneficial agent, macroparticulates and other desired excipients or other common tabletting methods.

Several different phase-inversion methods may be used to apply an asymmetric coating to the capsules or tablets (e.g., E.P.O. 0357369). These phase-inversion methods include the vapor quench process, the dry process, the liquid quench process, and the thermal process. Asymmetric membrane coatings can also be made by interfacial polymerization (e.g., E.P.O. Pub. No. 0357369).

In the vapor quench process, membrane formation is accomplished by penetration of a precipitant for the polymer into the solution film from the vapor phase, which may be saturated with the solvent used. A porous membrane is produced without a skin and with an even distribution of pores over the membrane thickness.

In the dry process, the polymer is dissolved in a mixture of a solvent and a poor solvent, of which the former solvent is more volatile. The polymer precipitates when the mixture shifts in composition during evaporation to a higher nonsolvent content. A skinned or nonskinned microporous membrane can be the result.

In the liquid quench process, film formation is caused by the immersion of the cast polymer film in a nonsolvent bath. The polymer precipitates as a result of solvent loss and nonsolvent penetration (exchange of the solvent with nonsolvent). A skinned or nonskinned membrane can be the result.

In the thermal process, a solution of polymer in a mixed solvent, which is on the verge of precipitation, is brought to phase separation by a cooling step. When evaporation of the solvent has not been prevented, the membrane can have a skin.

Microporous asymmetric coatings can also be made by inclusion of a leachable component in the coating formulation. For example, a small molecular weight sugar, salt, or water soluble polymer particles can be suspended or dissolved in the coating solution. Once the coating is applied, then the water-soluble materials can be leached out by immersion in water, forming a microporous asymmetric coating.

It should be understood that the invention is not limited to the particular embodiments shown and described herein, but that various changes and modifications may be made without departing from the spirit and scope of this invention concept as defined by the following claims.

EXAMPLE 1

Control of Initial Release Rate and Maximal Extent of Drug Release

Asymmetric membrane capsules were made by a phase inversion process in which the membrane was precipitated on a mold pin by dipping the mold pin in a coating solution followed by quenching in an aqueous solution. Thus, cylindrical stainless steel mold pins about 5.1 cm long with diameters that allowed the cast halves to snugly fit each other were used. They were first lubricated with a silicone fluid (Dow MDX4 Medical Grade Fluid, Dow Chemicals, Midland, Mich.) diluted in methylene chloride. The silicone fluid served as a release agent, i.e., it aided the stripping of the capsule half after drying. The mold pins were then dipped into a solution consisting of cellulose acetate/acetone/ethyl alcohol/glycerine citrate (15/49/28/8). This was followed by slowly withdrawing the mold pins from the solution and rotating them twice, to evenly distribute the polymer around the pins. As the polymer solution became increasingly viscous because of phase separation, it formed a capsular shape over the mold-pins. Then, the mold-pins were lowered into a 90/10 mixture of water/glycerine to quench. After about 15 minutes in the quench bath, the pins were withdrawn and allowed to dry at room temperature. After drying, the capsule shells were stripped off the pins by a stripping collar, trimmed to size with a razor blade, and the two halves joined. The cycle time from dipping to stripping was about 45 to 55 minutes.

Figure 2:
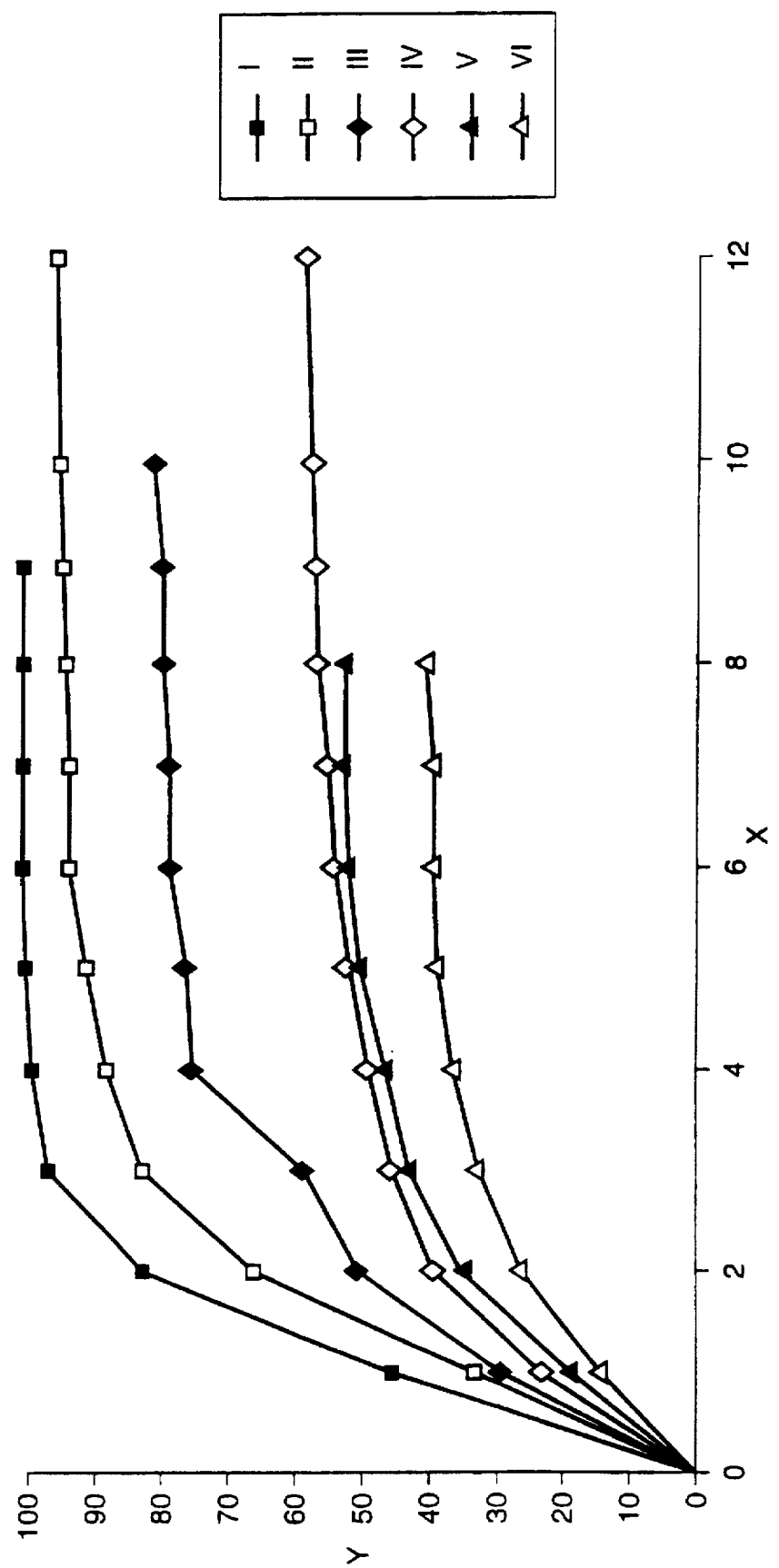
FIG. 2 is a graph of beneficial agent released from an asymmetric membrane coated capsule having uncoated excipients.

The body of the asymmetric membrane capsules was filled with 20 mg glipizide (approximately 12%), mixtures of TRIS (tromethamine, tris(hydroxymethyl)aminomethane, or THAM) and fructose in the proportions given in Table 1, and 0.5% magnesium stearate. The release profile of glipizide into 0.004M TRIS obtained with these formulations, labelled I through VI, is shown in FIG. 2. FIG. 2 graphs percent % glipizide released (Y) against time in hours (X) for the various formulations keyed to Table 1.

TABLE 1

Asymmetric membrane capsule formulations of Example 1

| Components | I | II | III | IV | V | VI |
|---|---|---|---|---|---|---|
| Glipizide | 12 | 12 | 12 | 12 | 12 | 12 |
| TRIS | 87.5 | 70 | 50 | 35 | 25 | 15 |
| Fructose | 0 | 17.5 | 37.5 | 52.5 | 62.5 | 72.5 |
| Magnesium stearate | 0.5 | 0.5 | 0.5 | 0.5 | 0.5 | 0.5 |
|  | 100% | 100% | 100% | 100% | 100% | 100% |

Glipizide was completely released from Formulation I containing TRIS as the major component (no fructose) over a 2 to 3 hour period. As the proportion of TRIS in the asymmetric membrane capsule formulation was reduced (and that of fructose was increased), the initial release rate of glipizide was reduced. Also the extent of release was progressively lower. Thus, the maximal extent of glipizide released decreased with a decrease in the TRIS content of the formulation.

Table 2 lists the initial release rate (calculated from the initial slope of the release profile), the maximal extent of glipizide released, and the time to release 90% of the maximal extent.

TABLE 2

Calculated release characteristics of glipizide formulations of Example 1

| Formulation | % TRIS | Initial Release Rate (%/hr) | Extent of Release (% of initial) | Time for 90% drug to be released (hr) |
|---|---|---|---|---|
| I | 87.5 | 44.8 | 100 | 2.6 |
| II | 70 | 32.2 | 97.5 | 4.0 |
| III | 50 | 29.4 | 82.5 | 4.5 |
| IV | 35 | 21.7 | 57.3 | 5.7 |
| V | 25 | 18.7 | 52.5 | 5.0 |
| VI | 15 | 13.9 | 39.2 | 4.0 |

This example demonstrates control of the initial release rate and the maximal extent of glipizide released from asymmetric membrane capsules by selecting the proper fill formulation.

EXAMPLE 2

Control of Time-lag Before Onset of Drug Release

Asymmetric membrane capsules were fabricated as described in Example 1 and were filled with a #60-100 mesh granulation consisting of glipizide/lactose/Klucel EF 15/80/5 (Klucel EF Hydroxypropylcellulose, Aqualon, Wilmington, Del.). The granulation was made by a standard aqueous wet granulation process. In addition to this granulation, the capsules were filled with 0.48 cm meglumine (sometimes referred to as N-methyl glucamine) tablets that were, in some cases, film-coated with a cellulose acetate/polyethylene glycol 1000 (M.W.) (CA/PEG) membrane. The coated meglumine tablets were made by wet granulating a 95/5 mixture of meglumine/Klucel-EF. A 9/1 mixture of magnesium stearate/sodium lauryl sulfate and colloidal silicon dioxide were added to the meglumine granulation and this blend was compressed into 0.48 cm tablets using the Type F (Manesty, Liverpool, England) tabletting machine. The meglumine tablets were spray film-coated at the 10% w/w core or 20% w/w core level with a 9/1 CA/PEG 1000.

Figure 3:
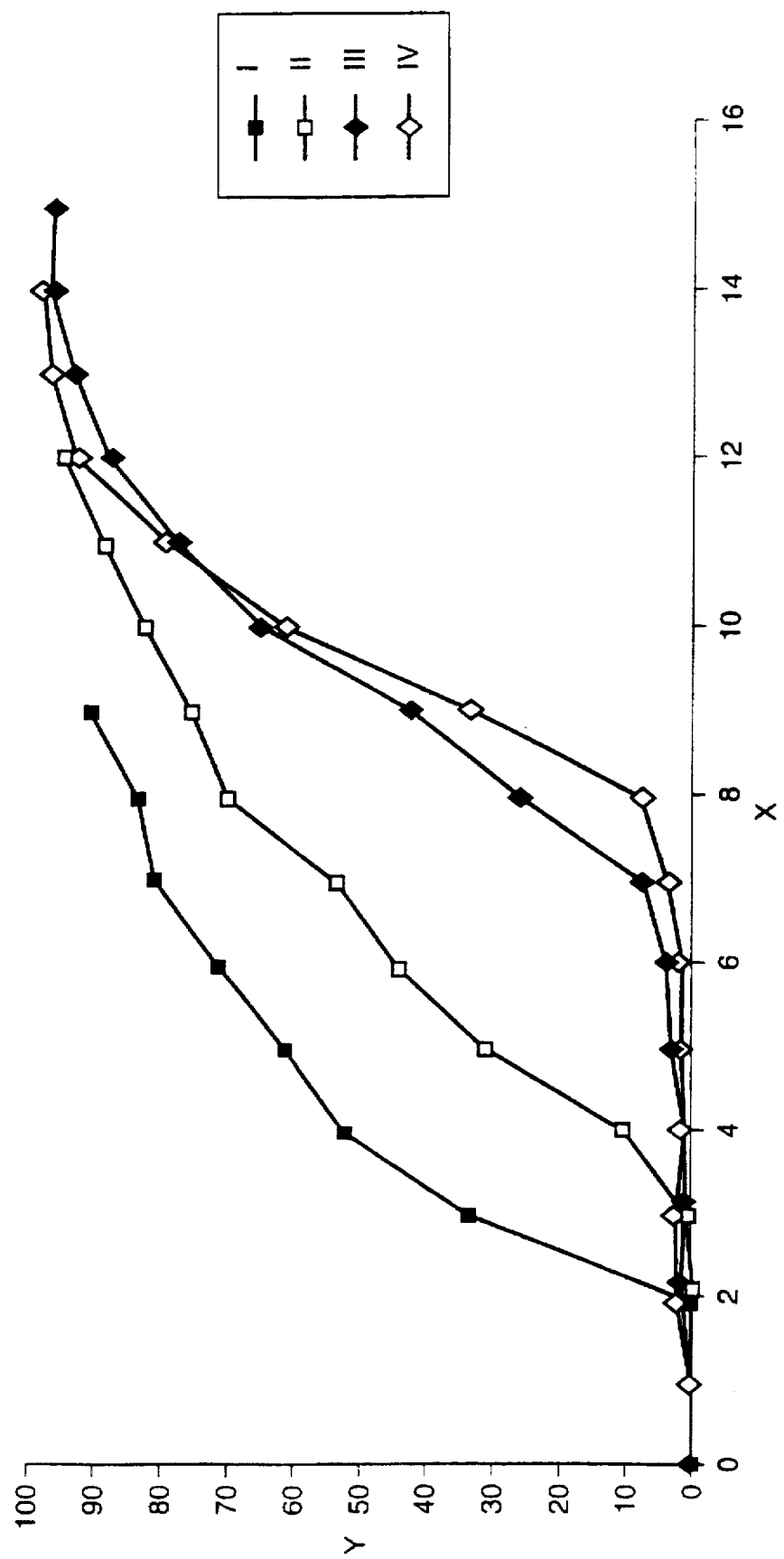
FIG. 3 is a graph of beneficial agent release from an asymmetric membrane coated capsule having coated excipients.

Glipizide release from these capsules showed a reproducible time-lag before the onset of release. The magnitude of this time-lag was dependent on the coating level relative to the core and on the ratio of CA/PEG in the filmcoat applied to the meglumine tablets (FIG. 3). FIG. 3 graphs percent % glipizide released (Y) against time in hours (X) for the various formulations keyed to Table 3. After the reproducible time-lag, drug release occurred at a relatively rapid rate that was characteristic of a capsule formulations containing glipizide and meglumine. The time-lag data are summarized in Table 3.

TABLE 3

Summary of time-lag observed before glipizide release from asymmetric membrane capsules containing a glipizide granulation and coated meglumine tablets

| Encapsulated Meglumine Formulation | Time-lag (hr) |
|---|---|
| I Uncoated meglumine tablets | 1 hour |
| II 2 meglumine tablets coated with a 6/4 CA/PEG membrane at a 10% (w/w core) level | 2 hours |
| III 2 meglumine tablets coated with a 9/1 CA/PEG membrane at a 10% (w/w core) level | 4 hours |
| IV 2 meglumine tablets coated with a 9/1 CA/PEG membrane at a 20% (w/w core) level | 6 hours |

This example demonstrates that time-lag can be controlled before the onset of drug release from asymmetric membrane capsules by filling the capsules with a drug granulation as well as an encapsulated excipient formulation. The magnitude of the time-lag can be controlled by selecting the coating level and the film coat surrounding the excipient tablet.

EXAMPLE 3

Control of the Shape of the Release Profile

Asymmetric membrane capsules consisting of cellulose acetate/acetone/ethyl alcohol/glycerine/triethylcitrate 15/49/28/3/5 were made by the process described in Example 1. They were then filled with formulations designated I through III shown in Table 4. Formulation I was made by a conventional aqueous wet-granulation method and sized to #60-100 mesh while Formulations II and III were made by blending, screening, and reblending.

TABLE 4

Asymmetric membrane capsule formulations of Example 3

| Components | I | II | III |
|---|---|---|---|
| Glipizide | 8.5 | 6.0 | 4.7 |
| Meglumine | 86.9 | 56.1 | |
| Klucel | 4.6 | | |
| Sodium bicarbonate | | 37.4 | |
| Tribasic sodium phosphate | | | 32.6 |
| Sodium chloride | | | 62.7 |
| Magnesium stearate | | 0.5 | |
| Total | 100.0 | 100.0 | 100.0 |
| Process description | Wet granulated and sized to #60-100 mesh | Blend-mill-blend | Blend-mill-blend |

Figure 4:
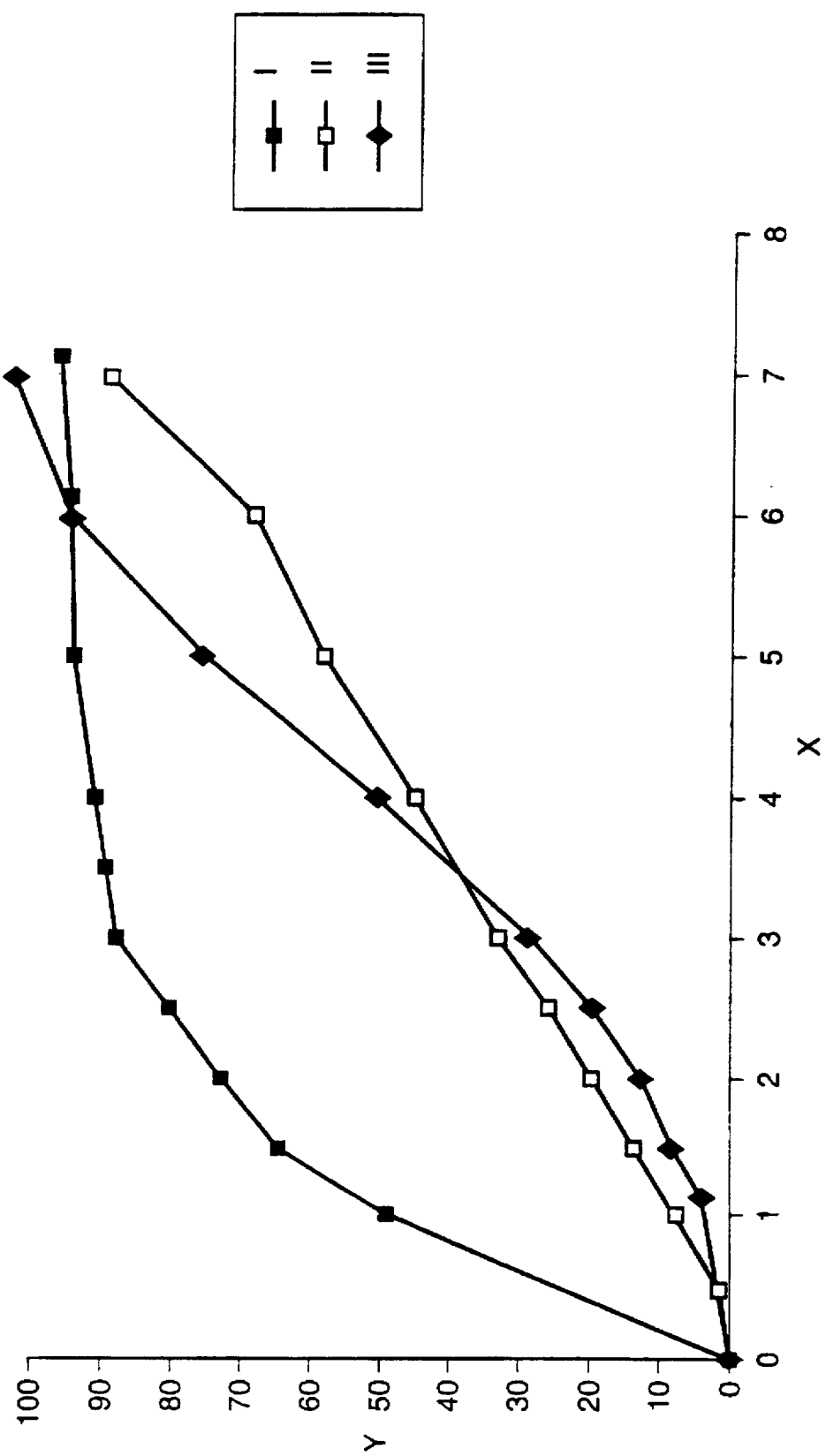
FIG. 4 is a graph of beneficial agent release from an asymmetric membrane coated capsule having uncoated excipients illustrating different release profiles.

The plot of the glipizide release profile observed with these formulations during most of the delivery period was respectively concave downwards, linear, and concave upwards for the formulations I through III (FIG. 4). FIG. 4 graphs percent (%) glipizide released (Y) against time in hours (X) for the formulations keyed to Table 4. The glipizide release rates were calculated as a function of time from the release profiles. These indicate a decreasing, constant, and increasing rate of glipizide release depending on the formulation used.

This example demonstrates that the shape of the drug release profile is dependent on the fill formulation used in asymmetric membrane capsules. Thus, decreasing, relatively constant, and increasing release rates are possible.

EXAMPLE 4

Combination of Incomplete Release and Time-lag Before Onset of Release

Asymmetric membrane capsules were made as in Example 3 and filled with the following:

(1) a glipizide granulation containing 9.5% glipizide, 20% TRIS, 70% lactose, and 0.5% magnesium stearate, and (2) one 0.48 cm meglumine tablet coated with a 9/1 cellulose acetate/polyethylene glycol-1000 (CA/PEG) coat at 10% (w/w core) level. The meglumine tablet itself was made by combining and compressing a meglumine granulation (93%), 9/1 magnesium stearate/sodium lauryl sulfate (5%), and colloidal silicon dioxide (Cabosil) (2%). The meglumine granulation was prepared by a wet-granulation of meglumine (95%) and hydroxypropylcellulose (Klucel) (5%).

Figure 5:
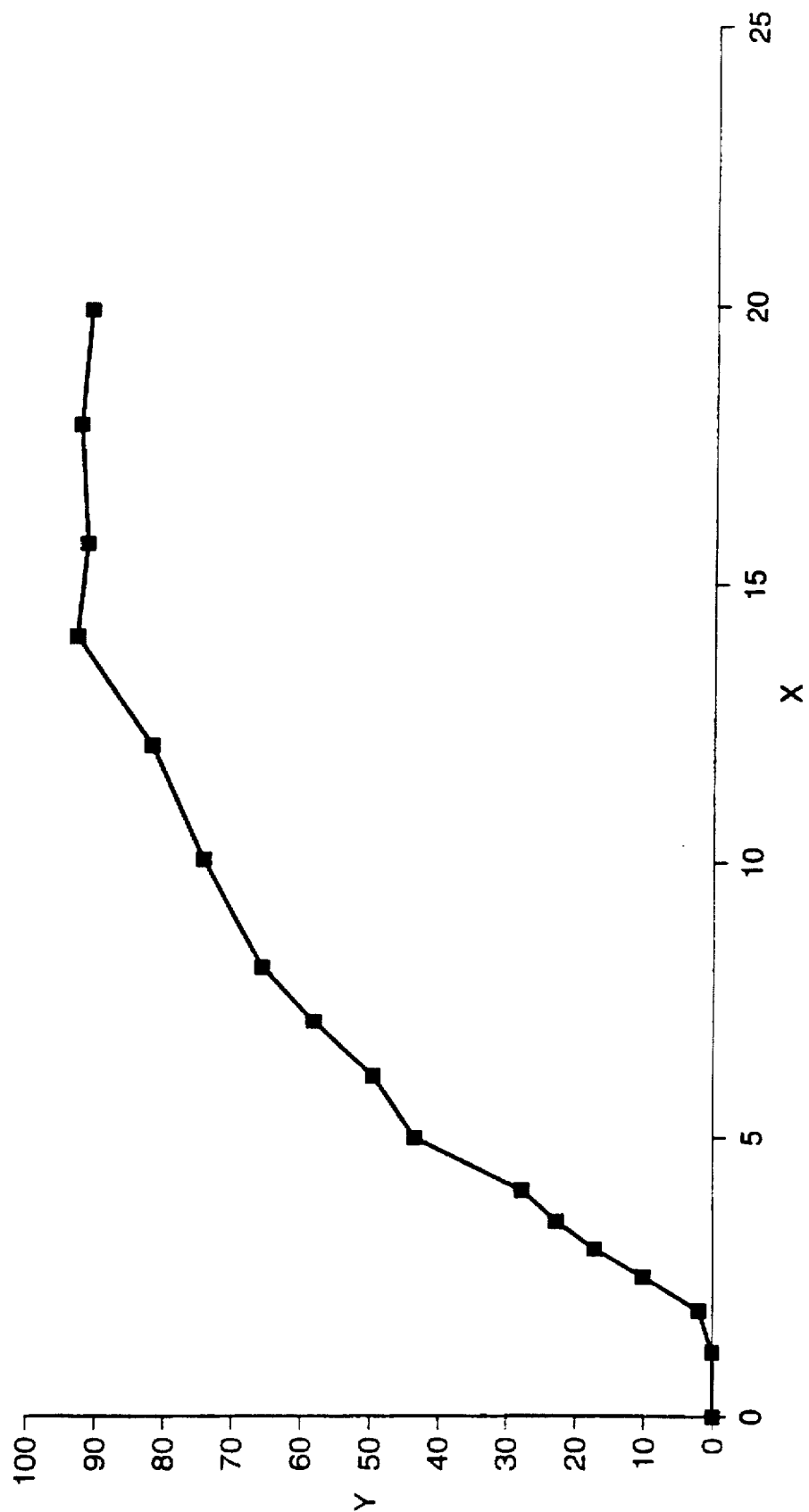
FIG. 5 is a graph of beneficial agent release from an asymmetric membrane coated capsule having a combination of coated and uncoated excipients.

Based on the results discussed in previous examples, the glipizide granulation, by itself, was expected to give the following release characteristics: initial release rate, 16.3%/hr; maximal extent of glipizide release, 46%; time for releasing 90% of the glipizide in this formulation, 4.5 hours. The encapsulated excipient formulation, by itself, was expected to give a time-lag of 4 hours before the onset of drug release. By combining these formulations, a sustained and complete release of glipizide over a prolonged period was achieved. The actual glipizide release profile obtained with this formulation is shown in FIG. 5. FIG. 5 graphs percent (%) glipizide released (Y) against time in hours. This example demonstrates that the different elements of programmed delivery can be combined in a dosage form to obtain release characteristics that were not otherwise possible. Thus, by combining, in an asymmetric membrane capsule, a formulation which, by itself, would have released incompletely but without a time-lag and another formulation which, by itself, would have given a time-lag but would have released all the drug load, it is possible to obtain a prolonged release of the drug.

EXAMPLE 5

Combination of Two Different Time-lags

Asymmetric membrane capsules were made as in Example 3 and filled with the following:

(1) a glipizide granulation containing 15% glipizide, 80% lactose, and 5% hydroxypropylcellulose (Klucel), (2) one 0.48 cm meglumine tablet coated with a 6/4 cellulose acetate/polyethylene glycol-1000 (CA/PEG) coat at 10% (w/w core) level. The meglumine tablet itself was made by combining and compressing a meglumine granulation (93%), 9/1 magnesium stearate/sodium lauryl sulfate (5%) and colloidal silicon dioxide (Cabosil) (2%). The meglumine granulation was prepared by a wet-granulation of meglumine (95%) and hydroxypropylcellulose (Klucel) (5%), and (3) one 0.48 cm meglumine tablet coated with a 9/1 cellulose acetate/polyethylene glycol-1000 (CA/PEG) coat at 20% (w/w core) level. The meglumine tablet itself was made by combining and compressing a meglumine granulation (93%), 9/1 magnesium stearate/sodium lauryl sulfate (5%) and colloidal silicon dioxide (Cabosil) (2%). The meglumine granulation was prepared by a wet-granulation of meglumine (95%) and hydroxypropylcellulose (Klucel) (5%).

Figure 6:
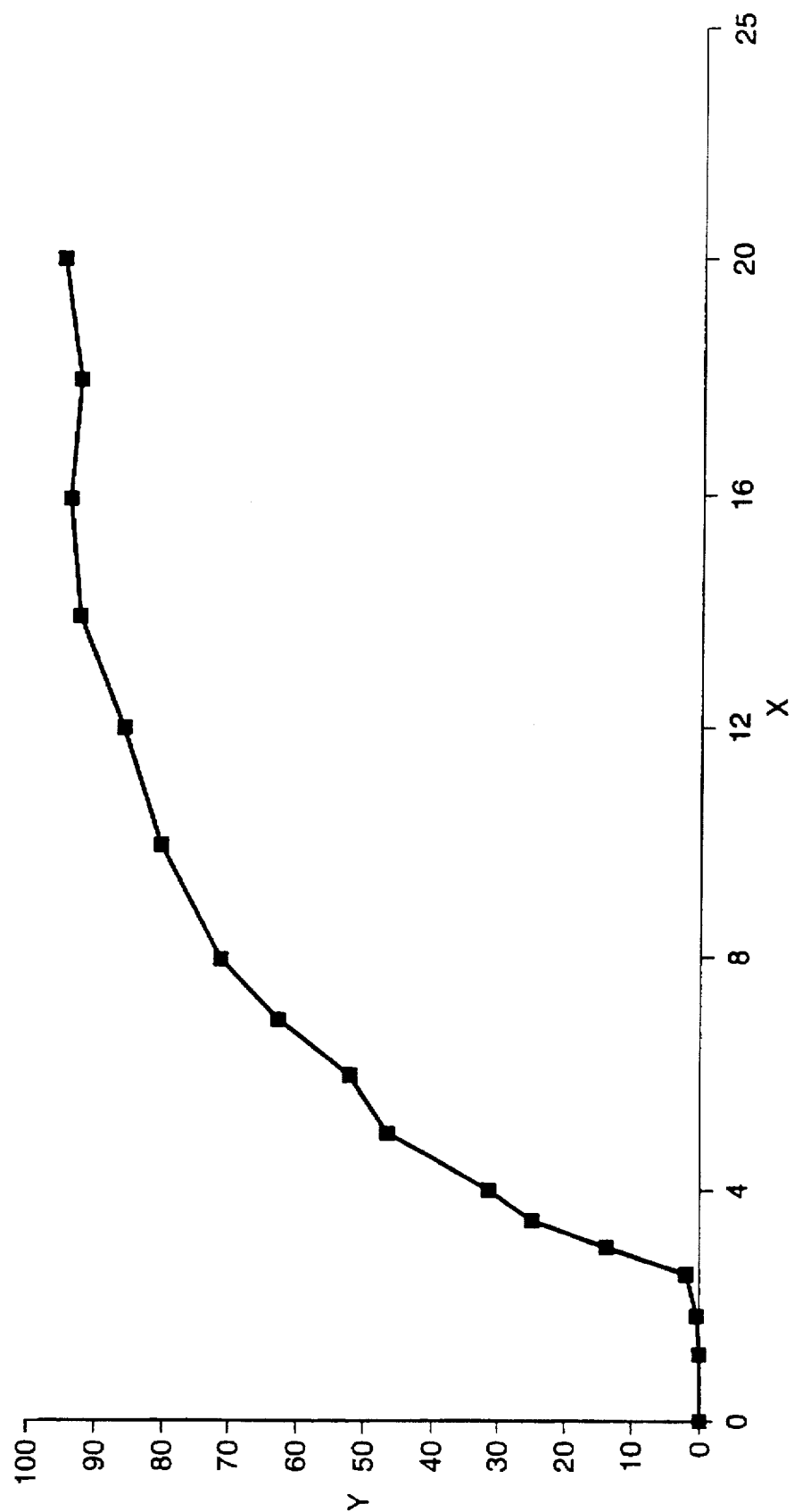
FIG. 6 is a graph of beneficial agent release from an asymmetric membrane coated capsule having coated excipients with different time lags.

The actual glipizide release profile obtained with this formulation is shown in FIG. 6. FIG. 6 graphs percent (%) glipizide released (Y) against time in hours (X). This example demonstrates that different elements of programmed delivery can be combined in a dosage form to obtain release characteristics in a more efficient manner.

I claim:

1. A capsule device for delivery of a beneficial agent to an aqueous environment comprising:

a. a beneficial agent, said beneficial agent is poorly soluble in the aqueous environment and is a pharmaceutical or veterinary agent;

b. an osmagent;

c. a macroparticulate solubility modifier that is selected to modify the solubility of the beneficial agent and thus provides a predetermined beneficial agent solubility and wherein said macroparticulate solubility modifier comprises compressed macroparticles and wherein said device includes uncoated solubility modifier;

d. said macroparticulate solubility modifier having a coating thereon, said coating peaceable to the aqueous environments, wherein said macroparticulate coating is a mixture of cellulose acetate and polyethyleneglycol and said coated macroparticulate solubility modifier being 0.16 cm to 1.27 cm in diameter wherein said macroparticulate contains a mixture of N-methyl glucamine and hydroxypropylcellulose; and e. an asymmetric membrane surrounding said beneficial agent, osmagent and macroparticulate solubility modifier wherein the device does not include a hydrogel and the coated macroparticulate solubility modifier does not include the beneficial agent.

2. The device as recited in claim 1 wherein said solubility modifier is an osmagent.

3. The device as recited in claim 1 wherein said solubility modifier is the osmagent.

4. The device as recited in claim 1 wherein said beneficial agent is the osmagent.

5. The device as recited in claim 1 wherein said macroparticulate coating has a duration sufficient to achieve release of substantially all the beneficial agent.

6. The device as recited in claim 1 wherein said device includes two macroparticulates, said macroparticulates having substantially different release time lags.

7. A method for the delivery of a beneficial agent to an aqueous environment of use which comprises placing the device of claim 1 into the aqueous environment of use.

8. The device as recited in claim 1 wherein said beneficial agent is highly soluble in the aqueous environment.

* * * * *